United States Patent [19]
Viebahn et al.

[11] Patent Number: 5,158,454
[45] Date of Patent: Oct. 27, 1992

[54] DENTAL UNIT

[75] Inventors: Renate Viebahn, Iffezheim; Ernst G. Beck, Wettenberg; Karl-Heinz Busch, Au/Rhein, all of Fed. Rep. of Germany

[73] Assignee: Dr. J. Hansler GmbH, Iffezheim, Fed. Rep. of Germany

[21] Appl. No.: 611,286

[22] Filed: Nov. 9, 1990

[30] Foreign Application Priority Data

Nov. 11, 1989 [DE] Fed. Rep. of Germany ....... 3937578

[51] Int. Cl.$^5$ ............................................. A61C 1/10
[52] U.S. Cl. ....................................... 433/82; 433/88; 433/98
[58] Field of Search ...................... 433/27, 98, 99, 100, 433/82, 88; 422/28, 1, 292, 305

[56] References Cited

U.S. PATENT DOCUMENTS

| | | | |
|---|---|---|---|
| 3,719,017 | 3/1973 | Shapiro et al. | 422/28 |
| 4,049,552 | 9/1977 | Arff | 422/305 |
| 4,216,185 | 8/1980 | Hopkins | 422/28 |
| 4,245,989 | 1/1981 | Folkenroth et al. | 433/27 |
| 4,545,956 | 10/1985 | Ciszewski et al. | 422/28 |
| 4,640,782 | 2/1987 | Burleson | 422/28 |
| 4,752,444 | 6/1988 | Bowen et al. | 422/292 |

Primary Examiner—John J. Wilson
Attorney, Agent, or Firm—Penrose Lucas Albright

[57] ABSTRACT

Apparatus for disinfecting water to make it virtually microbe-free and maintaining it in a continuous microbe-free condition for use at a center for dental instruments and the other apparatus by ozonized water. Water is ozonized and provided on both the dentist's side and dental assistant's side of a dental unit which includes a variety of dental instruments such as drills, syringes and an expectoration bowl. At least one water reservoir is connected through fluid conduits with such instruments. An ozone producing device is connected with the water reservoir and the ozone level in the fluid conduits between the water reservoir and the instrument center and apparatuses is controlled so that the ozone level at the water discharge openings at the dental instruments and other apparatus is zero or substantially zero. Ozone radical converters are incorporated in the fluid conduits at or immediately prior to the dental instruments or other apparatus which, for the syringes and expectoration bowl, convert ozone to oxygen and which also can be selectively inactivated.

13 Claims, 2 Drawing Sheets

DENTAL UNIT

FIELD OF THE INVENTION

This invention relates to apparatus to disinfect water which is used by dentists and dental assistants for dental instruments used at the dental working area. More particularly, the invention is for an apparatus which ozonizes tap water supplied to dental instruments for continuously disinfecting that water and selectively converting the ozone therein to oxygen prior to the discharge outlets for the water.

BACKGROUND OF THE INVENTION

Instrument centers for dentists, hereinafter called "dental units," incur significant microbe build-up at the water removal points for drills, turbines, syringes, and so forth. The source for this microbe build-up is commonly the tap water itself, or an ion exchange upstream in the system may be a breeding site for various types of microbes (bacteria, fungi, spores). The microbe source is most frequently, however, in the conduit system for the water, which include T-shaped and elbow sections. These conduits, with the customary and increasing use of plastic, provide excellent microbe growth media, particularly inasmuch as the component parts of the plastic conduit system can provide a nutritive base for microbes. Also, upon completion of dental treatment, that is when hand held tools (for instance, drills) are set down by the dentist or dental assistant, pathological microbes originating from patients can be easily drawn by a very slight vacuum into the conduit system. These microbes may include hepatitis A or B viruses, herpes viruses, HIV and so forth. Disinfection or sterilization filters, inversion osmosis devices and so forth represent other critical points for microbial growth.

Microbes which can become established and multiply in the water passages of dental units are predominantly pseudomonas aeruginosa, pseudomonades of the fluorescence group and legionellas; furthermore alcaligenes faecalis, flavonic bacteria and escherichia coli have also been detected (see BECK and SCHMIDT 1986, J. BORNEFF 1988, BOTZENHART and HEROLD 1988).

Lowering the microbe count to legally permissible levels with fewer than 100 colony-forming units/ml (KBE/ml) is possible, according to present practice, only by continuous disinfection and sterilization of the water. A one-time sterilization of the instrument by a chemical disinfecting agent or water vapor does not have a permanent disinfecting or sterilization effect, as microbes are always resupplied from the water or from the patient.

SUMMARY OF THE INVENTION

Disinfecting agents which kill or inactivate all of the microbes without leaving a residue, or which otherwise destroy microbes in water so it is nearly germ-free and may be considered "germ-free" in practical terms are not yet known. Traditional disinfecting agents are either $H_2O_2/Ag+$ or chlorination. Consequently, an object of the invention is to provide apparatus for a dental unit in which the water being used in the mouth of the patients, and alternately on the hands of the dentist and dental assistant, is on a continuing basis sufficiently germ-free so that it may be considered "germ-free" for all practical purposes, without the medium which lowers the microbe content being present at the water discharge, or only being present and detectable at a low and harmless concentration. This object is achieved by the instant invention with dental units comprising drills, turbines, ultrasonic units, syringes and like mechanisms, by providing at least one water reservoir which contains ozone in the water and which is connected with such equipment and other instruments by fluid lines. This system employs an ozone producer connected in the water circuit upstream from the water reservoir provided for sterilization of the water, and controls the ozone component in the water in such a manner so that at water discharge points, the ozone concentration is zero or nil.

Ozone is the strongest oxidation agent which may be used in practice. It effectively kills viruses, bacteria, fungi and also shows a sporicidal effect.

The concentration range required for disinfection is dependent upon:

1. The disintegration rate of the ozone in the aqueous medium, $$O_3 \rightarrow 3/2\, O_2$$

is defined by:
 a. temperature;
 b. water quality, ionic concentration and organic impurities; and
 c. the pH level.

2. The disintegration which occurs in the ozone during the flow of the $O_3$—containing water within the system, which is dependent upon:
 a. the length and diameter of the conduit system; and
 b. the material of which hoses, valves and operational parts are composed.

In addition to automatic and heterocatalytic disintegration, the ozone concentration is reduced by ozone drift arising from chemical reactions with materials at diverse concentrations of water content.

A concentration range of from 5 to 10 mg $O_3/1$ for a liter $H_2O$ has been proved effective in providing satisfactory disinfection.

Simultaneously, however, the ozone concentration at the water removal points according to requirements must be $^cO_3=0$ or $^cO_3 \geqq 0$.

EXAMPLE

Comparison of the disinfecting effect of ozone water and $H_2O_2$ in vitro at 20° C.

Test microbe: Pseudonomas aeruginosa.
Concentration: 3 * $10^9$ KBE/ml
Process: Quantitative suspension test wherein 100 ml of the disinfecting agent are incubated with 1 ml microbe suspension. Immediately, then after one minute and finally after five minutes, samples are removed and are analyzed for the number of microbes still present.
Concentration of the disinfecting agent:
Ozone water: 10 mg ozone/1 for each liter of water
$H_2O_2$: 50 mg $H_2O_2/1$ for each liter of water.
Table I shows the results.

The disinfecting effect occurs immediately with ozone water. The $H_2O_2$ behaves the same as the bidistilled water (twice distilled water). $H_2O_2$ is used as a control.

TABLE I

The disinfection effects of ozone water compared with $H_2O_2$ as a control and bidistilled water:

| INITIAL BACILLUS COUNT | | |
|---|---|---|
| OZONE WATER | $H_2O_2$ | BIDIST. WATER |
| $2 * 10^9$ KBE/ml | $2 * 10^9$ KBE/ml | $2 * 10^9$ KBE/ml |
| BEGINNING OF TEST | | |
| OZONE WATER | $H_2O_2$ | BIDIST. WATER |
| 0.0 KBE/ml | $4 * 10^9$ KBE/ml | $4 * 10^7$ KBE/ml |
| AFTER ONE MINUTE | | |
| OZONE WATER | $H_2O_2$ | BIDIST. WATER |
| 0.0 KBE/ml | $2 * 10^7$ KBE/ml | $2 * 10^7$ KBE/ml |
| AFTER FIVE MINUTES | | |
| OZONE WATER | $H_2O_2$ | BIDIST. WATER |
| 0.0 KBE/ml | $2 * 10^7$ KBE/ml | $2 * 10^7$ KBE/ml |

BRIEF DESCRIPTION OF THE DRAWINGS

Other objects, adaptabilities and capabilities of the invention will be appreciated as the description progresses, reference being had to the accompanying drawing in which.

DESCRIPTION OF THE PREFERRED EMBODIMENT

Figure 1:
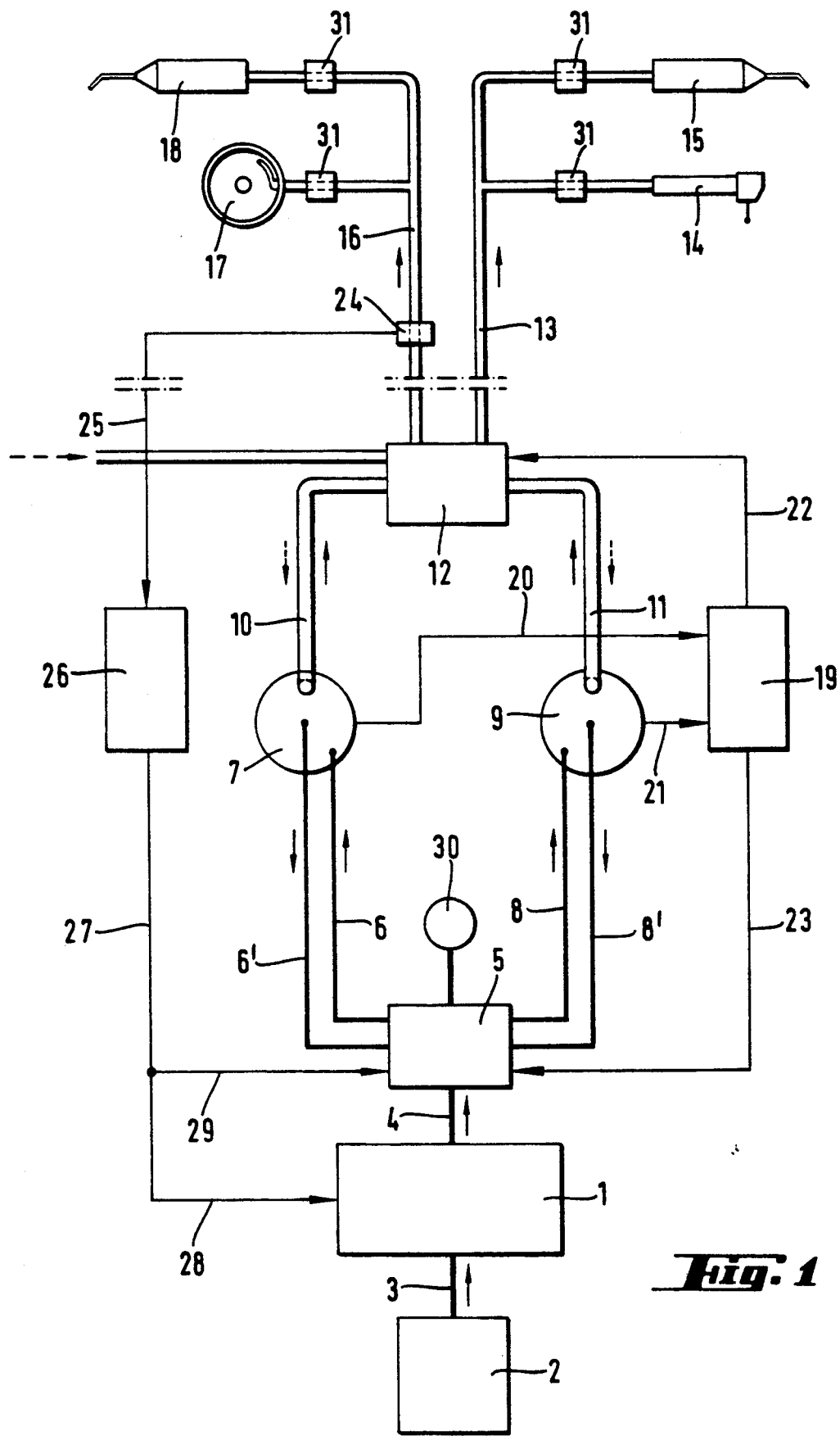
FIG. 1 is a diagrammatic representation of the invention.

A preferred embodiment of the invention, shows diagrammatically in FIG. 1, the water, gas ad control apparatus for a dental unit.

An ozone producing device 1 is supplied from conduit 3 with substantially pure oxygen or $O_2$ in air from an apparatus 2. The $O_2$ in air or oxygen is partially converted into ozone in the ozone producing device 1 and the ozone concentration may be adjusted in as gas ($^cO_3/1$ in a liter of gas mixture) and to be the same with the concentration in the water circuit ($^cO_3$ in mg of $O_3/1$ in a liter $H_2O$). From ozone producing device 1, the reaction gas is conducted through a gas conduit 4 to a control manifold 5 and discharged therefrom through a gas line 6 into a water reservoir 7 or through a gas line 8 into a further water reservoir 9. The required ozone concentration is dependent upon the method used and is in a range of five to fifteen mg $O_3/1$ in a liter $H_2O$. The reaction gas may serve simultaneously as compressed gas for water reservoirs 7 and 9. Lines 6' and 8' are feedback and recirculation lines for excess ozone.

Water ozonization occurs in alternate sequence in the illustrated example in each water reservoir 7 or 9 or in a group of such water reservoirs if more than two are provided, so that in the course of a processing cycle, at least one reservoir 7 or 9 is always available with ozonized water of the desired concentration for continuous disinfection and sterilization.

The ozonized water is discharged out of reservoir 7 through water line 10 and ozonized water from reservoir 9 is received by an ozone control manifold 12 through a water line 11. Manifold 12 provides, through a water line 13 on the dentist's side, water to the dental instruments, for example, a drill 14 or a syringe 15 and, through a further water line 16, to the other dental instruments on the side of the dental assistant, for instance, an expectoration bowl 17 and a further syringe 18.

A control unit 19 regulates the water level in reservoir 7 through an electric control circuit 20, and that of the reservoir 9 through another control circuit 21. A low water level in reservoir 7 or 9 is detected by control unit 19, which receives a signal that such condition exists through circuit 20 or circuit 21, whereupon a signal is transmitted to manifold 12 through a control circuit 22. Manifold 12 (in this example) is connected to a water supply network and upon receiving the signal indicating low water in reservoir 7 or reservoir 9, causes fresh water to be introduced via line 10 or line 11 to reservoir 7 or reservoir 9, as appropriate. Simultaneously or thereafter, control unit 19 initiates a command signal through a circuit 23 to control manifold 5 to commence supplying ozone into the just filled reservoir 7 or reservoir 9, as appropriate. Those skilled in the art will understand various alternate or substitute systems for obtaining and controlling water supplied to and discharged from reservoirs 7 and 9 within the scope of the instant invention.

A potentiometric detecting element 24 measures the $O_3$—concentration in line 16. The measured result is transmitted through an electric control circuit 25 to a control unit 26 which controls the $O_3$—concentration, by actuating ozone producing device 1 via control circuits 27 and 28, and control manifold 5 via lines 27 and 29. The ozone concentration is thus measured by potentiometric detecting element 24 which is located immediately prior to the dental instruments on the dental assistant's side. If this drops as low as $^cO_3 \leq 1$ mg of $O_2/1$ for a liter $H_2O$, then the other supply reservoir 9 (or one of the other supply reservoirs if more than two are provided) is connected into the unit's water system and regeneration and ozonization of the water is actuated. Detecting element 24 may also be operatively connected to line 13 on the side of the dentist, or the $O_3$—concentration may be measured in both lines 13 and 16, but it has been found from experience that when the system is in use, there are essentially no differences in measurements between the dentist's side and the assistant's side and thus, as a practical matter, a continuing measurement of the $O_3$—concentration need be made only in either line 13 or line 16.

A destructor system 30 which catalytically or otherwise destroys the ozone in excess reaction gas is connected to control manifold 5.

To provide an additional mechanism, for safety purposes, that removes excess ozone, built-in ozone radical converters 31 are provided in each line that carries ozone to a dental instrument or utensil such as drill 14, syringes 15 and 18, and bowl 17.

The system, according to the invention, provides that some $O_3$—water may be transmitted, if desired, to the water discharge points, either for disinfection of the expectoration bowl 17 at the assistant's side of the dental unit, or for oral disinfection or other therapeutic purposes on the dentist's side. Thus, the converters 31 for these discharge points may be selectively inactivated. On the other hand, for operational members, such as a turbine which turns drill 14, drinking water quality is to be guaranteed with $^cO_3 \leq 9.95$ mg $O_3/1$ for a liter $H_2O$.

Therefore, shortly prior the water discharge point, the ozone radical, insofar as it is still present, is converted by a converter 31 to $O_2$ free of any radicals. This may be accomplished, as desired, by means of the following $O_3$ conversion mechanisms:
a. thermally;
b. by ultrasound;
c. by means of microfilters;
d. catalytically (heterocatalytically);
e. by interconnecting micro-nozzles and atomizers; or
f. by any suitable combination of the above.

The ozone concentration at the water discharge points of an ozone-water-rinsed dental unit according to the invention has been tested using three different ambient temperatures (the measurements being by iodometric concentration). The results are set forth in Tables II, III and IV. These include the resulting measurements of water samples from five different removal points, each with and without an attached dental instrument.

The concentration measurement in the ozone water reservoir at the beginning and after 60 minutes served as control.

Table II (wherein the temperature is 15° C.) illustrates a method utilizing ozone, including removal or destruction of the ozone, occurring from water reservoir 7 or 9 and proceeding to the removal point, without being influenced by any operational member or any additional provision for ozone annihilation. Ozone use is 40% to 50% of capacity.

In Table III, the temperature, as specifically set forth in the Table, is 20° C.

According to Table IV (wherein the temperature is 25° C.) the ozone use is 50% to 70% of capacity. Ozone radicals are employed to disinfect dental tools. Ozone water is used for disinfection of the oral cavity, whereby converter 31 for the dentist's syringe is not activated.

TABLE II

Ozone concentrations at five different water discharge points of a dental treatment unit with and without a $O_3$ conversion mechanism:
Room Temperature: 15° C.

| | Removal Site | |
| --- | --- | --- |
| | Without Instrument Attached | With Instrument, $O_3$ Conversion Mechanism Activated Except for Syringe |
| Ozone Water Reservoir (immed.) | 14.16 mg $O_3$/1 $H_2O$ | |
| Syringe (dentist) | 6.96 mg $O_3$/1 $H_2O$ | 6.96 mg $O_3$/1 $H_2O$ |
| Turbine | 7.68 mg $O_3$/1 $H_2O$ | 0 mg $O_3$/1 $H_2O$ |
| 1st Micromotor | 7.20 mg $O_3$/1 $H_2O$ | 0 mg $O_3$/1 $H_2O$ |
| 2d Micromotor | 6.96 mg $O_3$/1 $H_2O$ | 0 mg $O_3$/1 $H_2O$ |
| Ultrasound | 8.40 mg $O_3$/1 $H_2O$ | 0 mg $O_3$/1 $H_2O$ |
| Ozone Water Reservoir (after 60 mins.) | 14.16 mg $O_3$/1 $H_2O$ | |

TABLE III

Room Temperature: 20° C.

| | Removal Site | |
| --- | --- | --- |
| | Without Instrument Attached | With Instrument, $O_3$ Conversion Mechanism Activated Except for Syringe |
| Ozone Water Reservoir (immed.) | 12.96 mg $O_3$/1 $H_2O$ | |
| Syringe (dentist) | 5.52 mg $O_3$/1 $H_2O$ | 5.52 mg $O_3$/1 $H_2O$ |
| Turbine | 6.72 mg $O_3$/1 $H_2O$ | 0 mg $O_3$/1 $H_2O$ |
| 1st Micromotor | 5.52 mg $O_3$/1 $H_2O$ | 0 mg $O_3$/1 $H_2O$ |
| 2d Micromotor | 5.28 mg $O_3$/1 $H_2O$ | 0 mg $O_3$/1 $H_2O$ |
| Ultrasound | 6.48 mg $O_3$/1 $H_2O$ | 0 mg $O_3$/1 $H_2O$ |
| Ozone Water Reservoir (after 60 mins.) | 12.72 mg $O_3$/1 $H_2O$ | |

TABLE IV

Room Temperature: 25° C.

| | Removal Site | |
| --- | --- | --- |
| | Without Instrument Attached | With Instrument, $O_3$ Conversion Mechanism Activated Except for Syringe |
| Ozone Water Reservoir (immed.) | 11.04 mg $O_3$/1 $H_2O$ | |
| Syringe (dentist) | 2.88 mg $O_3$/1 $H_2O$ | 3.12 mg $O_3$/1 $H_2O$ |
| Turbine | 5.76 mg $O_3$/1 $H_2O$ | 0 mg $O_3$/1 $H_2O$ |
| 1st Micromotor | 2.16 mg $O_3$/1 $H_2O$ | 0 mg $O_3$/1 $H_2O$ |
| 2d Micromotor | 2.16 mg $O_3$/1 $H_2O$ | 0 mg $O_3$/1 $H_2O$ |
| Ultrasound | 3.36 mg $O_3$/1 $H_2O$ | 0 mg $O_3$/1 $H_2O$ |
| Ozone Water Reservoir (after 60 mins.) | 10.56 mg $O_3$/1 $H_2O$ | |

The efficiency of the ozone disinfection and the superiority over $H_2O_2$ is demonstrated by Table I in the case of Pseudomonas aeruginosa. The drop in concentration to $O_3=0$ or $O_3>0$ if needed for disinfection purposes at the water removal points of a dental unit is demonstrated by Tables II to IV.

Parallel research carried out on two dental units demonstrated comparatively low effectiveness of disinfection with $H_2O_2/Ag+$. In this test, one unit was tested without water disinfection, while the other was operated with a continuous dosing of $H_2O_2/Ag+$. At all of the water removal points, five water samples were analyzed daily and a strong microbe build-up with circadian deviations was found (during the midday break for instance the microbe build-up increased greatly). The microbe count was one thousand times higher than the limit of one hundred KBE/ml required by local drinking water regulations.

Figure 2:
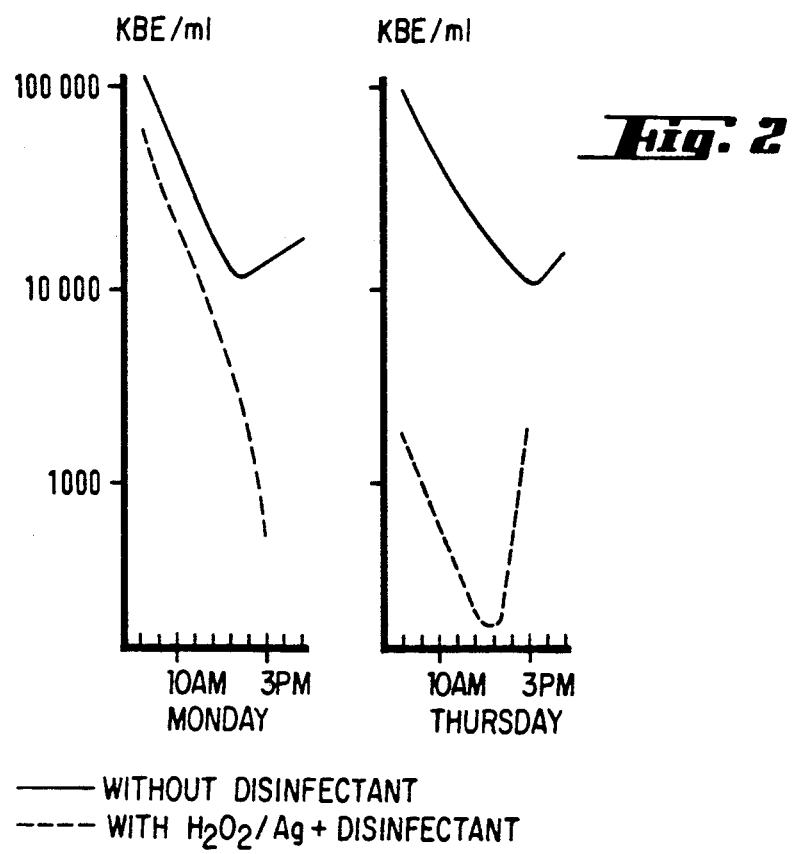
FIG. 2 illustrates in two graphs, microbe counts with and without a disinfection agent on a Monday and on a Thursday.

Differences are demonstrated in microbe count reduction with or without the disinfectant $H_2O_2/Ag+$, dependent upon the use, as illustrated in FIG. 2 which sets forth measurements taken on an hourly basis on a Monday and on a Thursday.

Table V, on the other hand, illustrates the effect of ozonized water as disinfection agent with $cO_3=10$ mg $O_3$/ml $H_2O$ on the microbe count for a dental unit following heavy microbe build-up over the weekend. At all five removal points, the microbe counts at and after 10 AM measurements are in the permissible range, according to local drinking water regulations.

TABLE V

Microbe count (KBE/ml) at discharge points on Monday between 8 AM and 5 PM with disinfection of a dental installation by ozone water.

| Removed Sample | Removal Time | | | | |
| --- | --- | --- | --- | --- | --- |
| | 8 AM | 10 AM | 1 PM | 3 PM | 5 PM |
| Syringe | 31760 | 19 | 5 | 2 | 0 |
| Turbine | 28 | 0 | 0 | 0 | 0 |
| 1st Micromotor | 17006 | 26 | 11 | 3 | 0 |

TABLE V-continued

Microbe count (KBE/ml) at discharge points on Monday between 8 AM and 5 PM with disinfection of a dental installation by ozone water. Removed Sample

| | Removal Time | | | | |
|---|---|---|---|---|---|
| | 8 AM | 10 AM | 1 PM | 3 PM | 5 PM |
| 2d Micromotor | 9608 | 2 | 0 | 0 | 0 |
| Ultrasound | 2706 | 9 | 1 | 0 | 0 |

Figure 3:
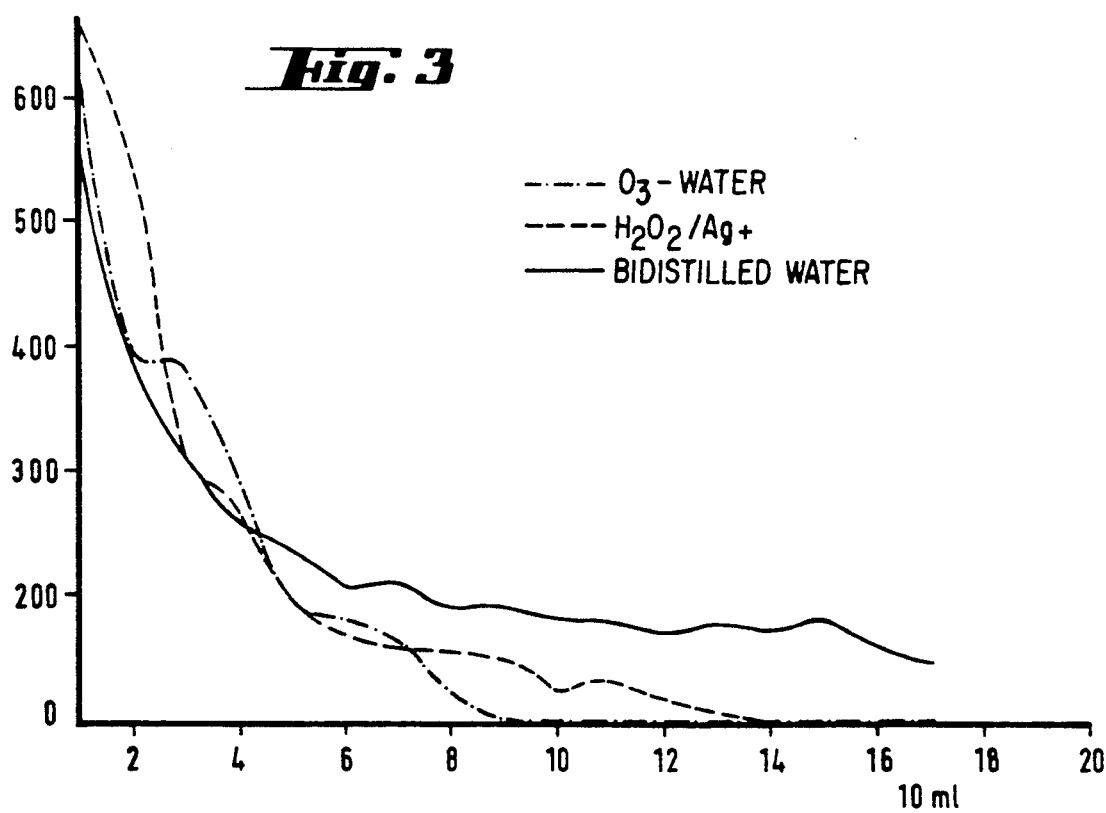
FIG. 3 illustrates three microbe counts taken from a dental basin that compares the use of ozone water, $H_2O_2/Ag+$ and bidistilled water.

The diagram in FIG. 3—also representing a Monday—illustrates the microbe counts obtained by simply draining off of the water volume (90 ml) left standing in the dental basin. With the use of ozone water, the microbe count drops almost immediately to zero, whereas with $H_2O_2/Ag+$ and bidistilled water, further rinsings are required.

Although the preferred embodiment of the invention is disclosed herein, it should be understood that it is capable of other adaptations and modifications within the scope of the appended claims.

Having fully described our invention, what we claim as new and to secure by Letters Patent of the United States is:

1. A dental unit comprising a center for dental instruments for use by a dentist and dental assistant, either individually or simultaneously, said center including water discharge openings for dental instruments and apparatus at said center such as turbines, drills, syringes and expectoration bowls, said dental unit further comprising at least one water reservoir connected by fluid conduits with said instruments, an ozone producing device connected with the water reservoir, said ozone producing device continuously providing sufficient ozone in said fluid conduits for effective microbe removal, and means for continuously controlling the ozone level in said fluid conduits between said water reservoir and said dental instruments and apparatus so that the ozone level at said discharge openings is zero or substantially zero.

2. A dental unit as claimed in claim 1, wherein said ozone producing device and said water reservoir are connected to a control manifold which, when said water reservoir is filled with water, causes said ozone producing device to produce ozone and controls and maintains a predetermined ozone concentration range in said water reservoir.

3. A dental unit as claimed in claim 2, wherein said center comprises a dentist's side and a dental assistant's side, and an ozone detecting element which signals the ozone concentration level existing at said element to a control unit which controls both said ozone producing device and said control manifold.

4. A dental unit as claimed in claim 2, wherein said control manifold is connected with said water reservoir through a filling conduit and a feedback conduit.

5. A dental unit as claimed in claim 2, comprising a control means which controls the water level in said water reservoir so that when the water level in said water reservoir drops below a predetermined water level, said control means signals information to such effect to an ozone control manifold, a supply source of water being connected to said ozone control manifold, said ozone control manifold upon receiving said information causing water from said supply source of water to be routed via a feedback conduit to said reservoir.

6. A dental, unit as claimed in claim 2, comprising a control means which also controls said control manifold.

7. A dental unit as claimed in claim 2, wherein an ozone destructor system is connected to said control manifold.

8. A dental unit as claimed in claim 1, wherein ozone detection units are connected into said fluid conduits on the dentist's side or the dental assistant's side or on both sides.

9. A dental unit as claimed in claim 1, wherein said ozone producing device is operatively connected to a device that provides said ozone producing device selectively with substantially pure oxygen or with air.

10. A dental unit as claimed in claim 1 comprising means for removing reaction gas from said ozone producing device and conveying said reaction gas in the form of compressed gas to said water reservoir.

11. A dental unit as claimed in claim 1, comprising at least two water reservoirs and means for removing ozonized water alternately out of each said reservoir while ozonized water is being supplied to the other said reservoir.

12. A dental unit as claimed in claim 1, comprising an ozone concentration of 5 to 15 mg $O_3/l$ for each liter of $H_2O$ supplied to said dental instruments and apparatus.

13. A dental unit in accordance with claim 1, wherein said means for controlling said ozone level comprises means for converting ozone to oxygen.

* * * * *